(12) United States Patent
Wimberger-Friedl et al.

(10) Patent No.: US 9,387,484 B2
(45) Date of Patent: Jul. 12, 2016

(54) MAGNETIC SAMPLE PURIFICATION

(75) Inventors: Reinhold Wimberger-Friedl, Veldhoven (NL); Remco Christiaan Den Dulk, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1049 days.

(21) Appl. No.: 13/500,446

(22) PCT Filed: Sep. 27, 2010

(86) PCT No.: PCT/IB2010/054330
§ 371 (c)(1),
(2), (4) Date: Jul. 2, 2012

(87) PCT Pub. No.: WO2011/042828
PCT Pub. Date: Apr. 14, 2011

(65) Prior Publication Data
US 2012/0270332 A1 Oct. 25, 2012

(30) Foreign Application Priority Data
Oct. 6, 2009 (EP) .................................... 09172326

(51) Int. Cl.
| G01N 1/28 | (2006.01) |
| H01F 1/00 | (2006.01) |
| G01N 35/00 | (2006.01) |
| B01L 3/00 | (2006.01) |
| B03C 1/01 | (2006.01) |
| B03C 1/015 | (2006.01) |
| B03C 1/28 | (2006.01) |

(52) U.S. Cl.
CPC . *B03C 1/01* (2013.01); *B03C 1/015* (2013.01); *B03C 1/288* (2013.01); *G01N 35/0098* (2013.01); *B01L 3/502761* (2013.01); *Y10T 436/25375* (2015.01)

(58) Field of Classification Search
CPC ..................... G01N 35/0098; B01L 3/502761; B03C 1/01; B03C 1/015; Y10T 436/25375
See application file for complete search history.

(56) References Cited

U.S. PATENT DOCUMENTS

| 3,796,660 A | 3/1974 | Kaiser |
| 3,926,789 A | 12/1975 | Shubert |
| 3,951,785 A | 4/1976 | Kaiser |

(Continued)

FOREIGN PATENT DOCUMENTS

| CN | 1950520 A | 4/2007 |
| CN | 101010592 A | 8/2007 |

(Continued)

OTHER PUBLICATIONS

Bayburtskiy, F.S. "Magnetic-Guided Carriers in Biological and Medical Investigations. A Review" Oxidation Communications, vol. 29, No. 3, pp. 529-544, 2006.

(Continued)

*Primary Examiner* — Christopher A Hixson

(57) ABSTRACT

A method and apparatus for extracting magnetic particles from a sample includes placing the sample near a liquid carrier, which is immiscible with it, in a configuration stable under the influence of gravity. The magnetic particles are moved by a magnetic field from the sample and into the carrier. The magnetic particles are non-wetting with respect to the carrier and will therefore form agglomerates in the carrier.

14 Claims, 3 Drawing Sheets

(56) References Cited

U.S. PATENT DOCUMENTS

| | | |
|---|---|---|
| 4,765,486 A | 8/1988 | Berlage |
| 6,121,055 A | 9/2000 | Hargreaves |
| 2007/0117212 A1 | 5/2007 | Kautz |
| 2007/0243634 A1 | 10/2007 | Pamula |
| 2008/0044893 A1 | 2/2008 | Pollack |
| 2009/0246782 A1 | 10/2009 | Kelso et al. |
| 2010/0041046 A1 * | 2/2010 | Chiu et al. .................. 435/6 |

FOREIGN PATENT DOCUMENTS

| | | |
|---|---|---|
| JP | 2003001243 A | 1/2003 |
| JP | 2011516034 A | 5/2011 |
| WO | 2007094739 A1 | 8/2007 |
| WO | WO 2009111316 A2 * | 9/2009 |

OTHER PUBLICATIONS

Hartshorne, Herb et al "Ferrofluid-Based Microchip Pump and Valve" Sciencedirect, Sensors and Actuators B. vol. 99, 2004, pp. 592-600.

Zhang, Chunsun et al "Micropumps, Microvalves, and Micromixers within PCR Microfluidic Chips: Advances and Trends" Sciencedirect, Biotechnology Advances, vol. 25, 2007, pp. 483-514.

* cited by examiner

MAGNETIC SAMPLE PURIFICATION

FIELD OF THE INVENTION

The invention relates to a method, an apparatus, and a kit for processing a liquid sample, particularly for extracting magnetic particles from said sample.

BACKGROUND OF THE INVENTION

The US 20070243634 A1 discloses a droplet microactuator with which single droplets of an emulsion can be manipulated. In a particular embodiment, magnetic beads that are contained in a droplet are immobilized at a surface of the device by a magnetic field. Another droplet can then be moved to their location, thus allowing to transfer the magnetic beads from one droplet to another. The mentioned apparatus is however rather complicated and hence not suited for many applications.

SUMMARY OF THE INVENTION

Based on this situation, it was an object of the present invention to provide simplified means for separating components of a sample liquid.

This object is achieved by a method according to claim 1, an apparatus according to claim 5, and a kit according to claim 11. Preferred embodiments are disclosed in the dependent claims.

According to a first aspect, the invention relates to a method for extracting magnetic particles from a liquid sample. In this context, the term "magnetic particle" shall comprise particles that are permanently magnetic as well as magnetizable particles, particularly micro-particles or nano-particles (i.e. particles having at least one dimension ranging between 3 nm and 5000 nm, preferably between 50 nm and 1000 nm). The liquid sample may particularly be of biological origin, for example blood or saliva. The method comprises the following steps, which may be executed at least once in the listed sequence:

a) Arranging the liquid sample from which magnetic particles (if present) shall be extracted adjacent to a liquid carrier, wherein this carrier is immiscible with the sample. The carrier may for example be lipophilic while the sample is hydrophilic (or vice versa). Furthermore, the carrier shall have another mass density than the sample, and the arrangement of sample and carrier shall be such that it is stable under the influence of gravity. In this context, the "influence of gravity" shall comprise any forces related to the mass of a body, i.e. gravitational attraction in the narrower sense as well as inertial forces like a centrifugal force. Due to the difference in mass densities and the immiscibility of the sample and the carrier, these liquids can be arranged adjacent to each other in a stable manner without mixing. Preferably, the sample and the carrier are present as two continuous phases (i.e. not in a form in which one is dispersed in the other).

b) Generating a magnetic field that moves magnetic particles contained in the sample from the sample into the carrier. To this end, the magnetic field will typically have a nonzero gradient by which a force is exerted on the dipoles of the magnetic particles.

By moving magnetic particles from the sample into a carrier, it is possible to extract only the magnetic particles from the sample while all other substances (impurities) are left behind. Hence a purification of the magnetic particles from the remainder of the sample is possible. Alternatively, the separation of magnetic particles from the sample may be done if one is actually interested in a sample without magnetic particles, for example because they are bound to poisonous substances. In any case, the method is simple because it does for example not require a movement of single sample droplets. Moreover, magnetic particles are transferred into the carrier directly via the interface between the carrier and the sample, which are kept in a stable arrangement under the influence of gravity. Hence there is no need to intermediately attach the particles or droplets of the sample or carrier to some surface. This accelerates the procedure and avoids possible problems due to a contact of e.g. magnetic particles to a surface. Finally, the method can be made very fast by providing a sufficiently large interface between the sample and the carrier, which may be present in two large (non-dispersed) phases.

The volume of the carrier phase may typically range between 0.01 and 1 ml depending on the device design and is determined by other design criteria for the device and user convenience. The volume of the sample can typically range between 0.01 and 100 ml depending on the analytical question. For a high sensitivity in bioanalytical assays the sample volume has to be chosen high. It is a particular advantage of the present method to be able to concentrate magnetic particles from a large volume into a small volume as a result of the clustering of the particles in the carrier medium. The volume of the carrier medium can be chosen largely independent of the sample volume. The effective volume of the cluster of magnetic particles which needs to be transported by the carrier phase depends only on the number and size of the particles and is independent of the sample volume and the carrier volume. Therefore very high concentration factors and purification factors can be achieved with the present method. In typical cases, the ratio between (a) the initial sample volume (with magnetic particles) and (b) the volume of magnetic particles (clusters) that were extracted from said initial sample may range between about 5:1 and about 1000:1, preferably between about 50:1 and about 500:1.

It should be noted that the magnetic particles will in many cases be bound to target components (e.g. biomolecules) of the sample. The method can then be used to extract said target components from the sample, which is achieved via the magnetic particles. This important application is always comprised by the following description even if only the movement of magnetic particles will be mentioned.

In many applications, the enrichment of magnetic particles in the carrier will only be an intermediate step for separating them from impurities and/or the sample. According to a particular embodiment of the invention, it is hence preferred that the magnetic particles are further on moved from the carrier into another material, for example a solution with reagents. The transition of the magnetic particles into the other material can be achieved in different ways, for example by sedimentation and/or forcibly by suitable magnetic fields.

In another embodiment of the invention, the magnetic particles are aspirated from the carrier (after they have been collected there) into some transfer device, for example a syringe or a pipette. The magnetic particles may then for example be dispensed from the transfer device into another solution.

To make the separation between the sample and the magnetic particles persistent, the sample may optionally be removed after the magnetic particles have been transferred into the carrier. In this case, further processing of the magnetic particles can be done in the same container as the previous separation step.

According to a second aspect, the invention relates to an apparatus for extracting magnetic particles from a liquid sample. The apparatus comprises the following components:

A "sample chamber" in which a liquid sample can be provided. The sample chamber is typically an empty cavity; it may be an open cavity, a closed cavity, or a cavity connected to other cavities by fluid connection channels.

A "carrier chamber" in which a liquid carrier that is immiscible with the sample and that has another mass density than the sample can be provided, wherein the carrier chamber is open to the sample chamber at an interface which will be called "inlet interface" in the following. Furthermore, the design of the chambers and the inlet interface shall be such that the sample and the carrier can assume a stable arrangement under the influence of gravity and that they contact each other at the inlet interface in this arrangement. In the usual or standard operating positioning of the apparatus, for example standing on a laboratory desks, the inlet interface will typically be oriented horizontally.

A magnetic field generator, e.g. a permanent magnet or an electromagnet, for generating a magnetic field that can move magnetic particles from the sample chamber into the carrier chamber. Preferably at least a component of this movement is parallel to the direction of gravity. The magnetic field of the field generator will typically have a configuration with a magnetic field gradient pointing from the sample chamber towards the carrier chamber.

The described apparatus allows to execute a method of the kind described above. Reference is therefore made to the above description of the method for more information on the details, advantages and modifications of the apparatus.

According to a preferred embodiment of the apparatus, the carrier chamber is pre-filled with a liquid carrier. This facilitates the application of the apparatus as one handling step is transferred from the user to the manufacturing site, where it can be executed with high precision and reproducibility. The user then merely has to fill the sample chamber with the sample at hand.

In another embodiment of the apparatus, the sample chamber and the carrier chamber are separated by a plane that comprises the inlet interface. When the apparatus is positioned such that the inlet interface is horizontal, the sample chamber will hence be completely above said plane while the carrier chamber is completely below said plane or vice versa. Immiscible liquids in the sample chamber and the carrier chamber can then stably arrange one above the other according to the influence of gravity. It should be noted that (small) deviations from a geometrically strict planarity of the inlet interface and the considered plane shall be allowed to take the influence of surface tension into account (which may cause some bending of interfaces at borders).

According to another embodiment of the apparatus, the carrier chamber is open to a third chamber at an interface that will be called "outlet interface" in the following. In this design, magnetic particles that were taken up by the carrier through the inlet interface can be released into the third chamber through the outlet interface, thus realizing a purification process in which (only) magnetic particles are transferred from the sample chamber via the carrier chamber into the third chamber.

The inlet interface and the outlet interface may preferably be parallel to each other (apart from small deviations due to surface tension effects), most preferably they may be located in a common plane.

To avoid the ingression of a liquid into the "wrong" chamber, for example of sample into the carrier chamber, it is preferred that the (inner) surface of the sample chamber is at least partially repulsive to the carrier and/or that the (inner) surface of the carrier chamber is at least partially repulsive to the sample. The carrier chamber may for example have a hydrophobic coating to repel an aqueous sample.

In a preferred embodiment of the invention that relates both to the method and the apparatus, the movement of the magnetic particles from the sample (or sample chamber) into the carrier (or carrier chamber) has at least a (vectorial) component that is parallel to the direction of gravity. To this end, the magnetic field that is generated will typically have a nonzero gradient by which a force is exerted on the dipoles of the magnetic particles, said force having a component in the direction of gravity. Preferably, more than 50%, more preferably more than 80%, and most preferably approximately 100% of the force are parallel to the direction of gravity. It should be noted that the parallelism leaves it open if the magnetic force pulls the magnetic particles in the same or in the opposite direction as gravity. Moving the magnetic particles parallel to the direction of gravity has the advantage that the arrangement of the sample and the carrier is not (or hardly) affected by this movement as it is stabilized by gravity. Hence there is no need for fixing the sample and/or the carrier by additional measures like an immobilization at a surface.

In another optional embodiment of the method or the apparatus, the magnetic particles can be moved by a magnetic field through the carrier to a target zone. The target zone may for example be the abovementioned outlet interface between the carrier chamber and a third chamber. The magnetic field may optionally be generated with the same magnetic field generator that moved the magnetic particles from the sample into the carrier, or with a different one.

According to a third aspect, the invention relates to a kit with chemical agents for processing a liquid sample, the kit comprising the following components:

Magnetic particles.

A liquid carrier that is immiscible with the sample and that has another mass density than the sample.

The kit provides materials that can be used for executing a method of the kind described above. Reference is therefore made to the above description of the method for more information on the details, advantages and modifications of the kit.

In the following, further developments of the invention will be described that apply to the method, the apparatus, and the kit according to the invention.

The higher the difference in mass density between the sample and the carrier, the more stable their separation will be under the influence of gravity. Hence the ratio of the mass densities will preferably be larger than 1:1.05, more preferably be larger than 1:1.15, most preferably be larger than 1:1.3

The carrier may particularly have a higher mass density than the sample, such that the sample will float upon the carrier in a stable configuration. Typically, the mass density of the carrier is higher than that of water.

The liquid carrier may comprise a large variety of materials, wherein the particular choice will typically depend on the requirements of an intended application. In a preferred embodiment, the carrier may comprise or consist of at least one of the following materials: halogenated oils, particularly fluorocarbons or perfluorocarbons (e.g. 3M Fluorinert® liquids); silicone oils; fluorosilicone oils; hydrocarbons, including aliphatic and aromatic hydrocarbons; alkanes. In biological applications, fluorocarbons are particularly advantageous as they are compatible to many biological materials, are hydrophobic, and have a higher mass density than aqueous solutions.

In another preferred embodiment, the magnetic particles used in the method, the apparatus, or the kit are non-wetting with respect to the corresponding carrier. This can for example be achieved by an appropriate choice of the (surface) material of the magnetic particles, for example by a hydrophilic surface material if the carrier is hydrophobic or vice versa. Magnetic particles that have been transferred into the carrier under the active influence of a magnetic field will then stick together and form agglomerates in the carrier. This has the advantage that the magnetic particles can be manipulated within the carrier in larger quantities, and for example collectively and completely be removed from the carrier by a pipette.

The magnetic particles may preferably be adapted to specifically bind target components in the sample, for example biological substances like biomolecules, complexes, cell fractions or cells, viruses or fractions of viruses, tissue extract etc. The magnetic particles can then be used as a label for such target components one is actually interested in. In this way the present invention can for example be applied for the selective extraction of virtually any component from a sample.

The invention further relates to the use of the apparatus and the kit described above for molecular diagnostics, biological sample analysis, chemical sample analysis, food analysis, and/or forensic analysis. Molecular diagnostics may for example be accomplished with the help of magnetic particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DESCRIPTION OF PREFERRED EMBODIMENTS

Figure 1:
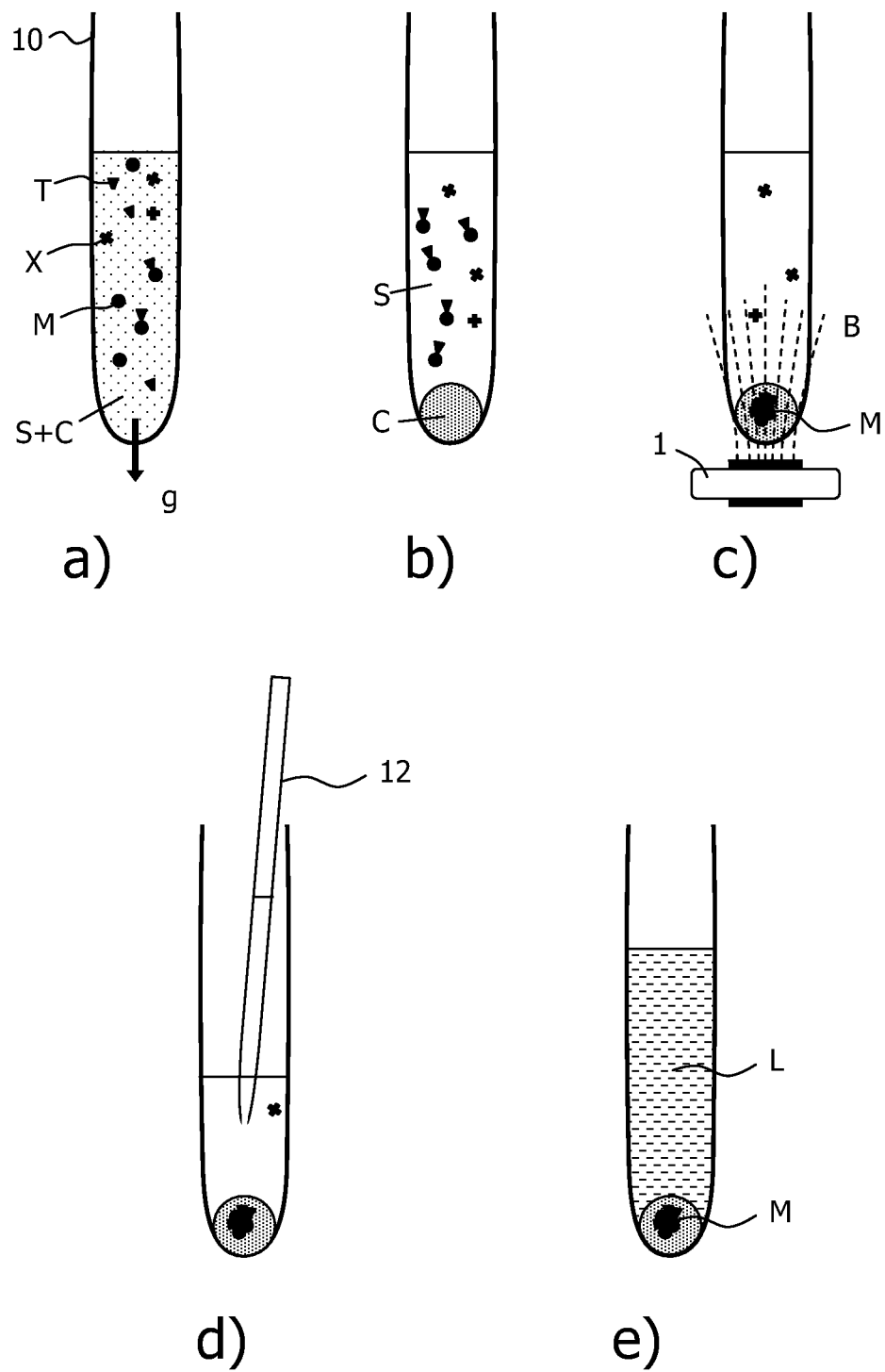
FIG. 1 illustrates consecutive steps of a first embodiment of a method according to the invention.

In the following, the present invention will be described with respect to the manipulation of biological materials, though it is not limited to such applications.

In many molecular diagnostics assays, DNA needs to be collected from samples and amplified before it can be detected. Amplification usually occurs with methods known as PCR reaction, RCA or NASBA. In these procedures, the matrix in which the target DNA is present must not inhibit or in other ways deteriorate the intended reactions. However, samples coming from patient material have a complex composition and the DNA is enclosed in cells which need to be lysed in order to make it accessible. Depending on the sample type and analytical challenge, the composition of the crude lysate is not compatible with e.g. PCR conditions in most cases. Therefore cleaning steps often combined with a concentration step have been introduced, like the well-known Boom method. There chaotropic salts, like Gu-SCN are added in high concentrations and the mixture is pumped through a silica membrane which binds the DNA to its surface. All salts, proteins and other contaminants can be washed away before the DNA is released again from the membrane by an elution buffer and introduced into the PCR reaction. Since also the chaotropic salts inhibit the PCR, washing has to be done carefully. In order to avoid the premature release of bound DNA during washing, non water-based solvents are used, like ethanol or acetone. Since these solvents interfere with PCR, they are removed by evaporation or centrifugation before DNA elution.

In general, the procedure of removing interfering substances from a matrix as well as replacing the matrix (i.e. solvent) for an improved biochemical reaction is referred to as "washing". The described PCR example illustrates that washing is crucial, but that washing steps take time and introduce errors due to uncontrolled volumes removed and/or left behind. Hence any measures which can be taken to reduce the number of washing and dispersion steps and the number of solvents and solutions are very desirable for low cost robust assays and devices.

To address these issues, a new principle for carrying out washing is proposed here. This principle comprises the use of actuated magnetic particles (called beads in the following) and a liquid carrier that is immiscible with the sample liquid. The magnetic beads may particularly be used for selectively capturing cells before lysis or DNA after lysis.

To explain the aforementioned principle in more detail, a preferred example will now be considered in which a fluorocarbon liquid (FC) is used as a carrier. The FC has a much higher density than water-based biological samples and is totally immiscible with them. Magnetic beads and FC may be added to a sample and mixed. After cessation of active mixing, the FC sediments form a continuous layer at the bottom. The magnetic beads, which are typically at least partially bound to selective target components, remain in the aqueous phase, i.e. the sample. By introducing a magnet, the beads are pulled into the FC layer. When the bead surface is incompatible with the FC matrix, the beads stay in the FC layer in a very compact fashion even when the magnet is removed. As a result, the beads and the targets bound to them are in a clean environment. No contaminating species will get from the sample into the FC phase, and no additional washing step is required.

Fluorocarbons that are suited for the described method (e.g. FC40 Fluorinert® from 3M with a mass density of about 1850 kg/m$^3$) have an advantageous behavior in combination with water-based solutions. They are immiscible and when mixed separate immediately, with the FC phase coalescing immediately at the bottom of the container.

Furthermore, magnetic beads that are typically used in bio-applications do not disperse in FC but in water. The magnetic beads may for example be superparamagnetic beads composed of ferromagnetic grains (e.g. of iron-oxide $Fe_2O_3$) embedded in a polymeric matrix (e.g. polystyrene), the size of the grains being below the superparamagnetic diameter, for example being around 5 nm to 15 nm. Upon actuating such magnetic beads with a magnet, the beads move towards the magnet and are for example collected at the wall of the container. From the wall of the container this cluster or agglomerate can be moved along the wall from the water to the FC phase. Once in the FC phase, the beads remain agglomerated even if the magnet is removed. This agglomerate can be aspirated by a pipette together with the FC without any loss. Upon addition of a water-based solution and shaking, the beads immediately disperse in the water phase without any loss in the FC phase. This means that a very convenient on the bench procedure can be employed, without washing steps and the loss of beads. Since the bead agglomerate can be completely and easily removed from the container, it can be transferred to a new container without loss and in this way also impurities which tend to stick to the wall of the container are removed efficiently.

FIG. 1 schematically illustrates the following consecutive steps of the aforementioned procedure:

a) Mixing a sample S, a carrier C (e.g. a fluorocarbon), and magnetic particles M in a sample chamber, which is realized here by a test tube 10. The sample S comprises the target components T one is interested in, e.g. DNA strands, wherein said target components T can specifically bind to the magnetic particles M. Moreover, the sample comprises a variety of further substances (impurities) which are summarized by the symbol X.

b) As the sample S and the carrier C are immiscible and as the carrier C has a higher density than the sample, the carrier C will eventually separate under the influence of gravity g and collect at the bottom of the sample chamber 10. It should be noted that this process might also take place in a centrifuge to accelerate it and/or to exploit smaller differences in mass density.

c) The magnetic particles M are moved from the sample S into the carrier C with the help of the magnetic field B (having a nonzero gradient) that is generated by a magnet 1 close to the carrier. During the resulting migration of the magnetic particles M, the sample and the carrier phases remain at their places as their arrangement is stably determined by the influence of gravity. As the magnetic particles are non-wetting with respect to the carrier, they form a cluster or agglomerate in the carrier phase. Due to the stability of this agglomerate, the magnet may be removed or switched off once the magnetic particles are in the carrier.

d) The sample is aspirated with a pipette 12, leaving behind the carrier C with the agglomerate of magnetic particles M.

e) Finally, the test tube 10 can be filled with the next aqueous reagent L to continue the intended procedure with the magnetic particles M and/or the target components T bound to them.

Figure 2:
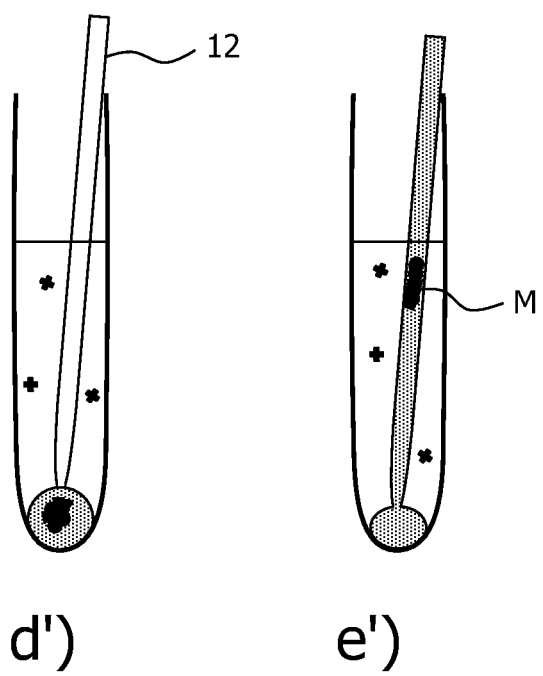
FIG. 2 illustrates consecutive steps of a second embodiment of a method according to the invention.

As an alternative to step d), the bead cluster M in the carrier C can be removed with a pipette 12 from the carrier layer without contamination from the sample S and introduced in another clean container (not shown) to continue the assay. This is illustrated in FIG. 2, in which steps a), b), and c) are identical to FIG. 1. However, steps d') and e') comprise the removal of the agglomerate of magnetic particles M from the carrier C with the help of a pipette 12. Typically, also at least some of the carrier C will be aspirated by the pipette 12 in this step. The possibility to take up a macroscopic volume of magnetic particles M is a unique feature of this approach. Due to the incompatibility of the magnetic beads M and the carrier C, the beads remain in a compact cluster and do not adhere to the walls of the tubes and pipettes so that nothing is lost.

In an integrated apparatus, the magnetic beads may be collected in a similar way by exposing them to a magnetic field through the substrate. First the FC phase and water phase need to be separate. This can be achieved in an integrated sample container, wherein the bottom of the container can have a channel which connects to a microfluidic environment.

Figure 3:
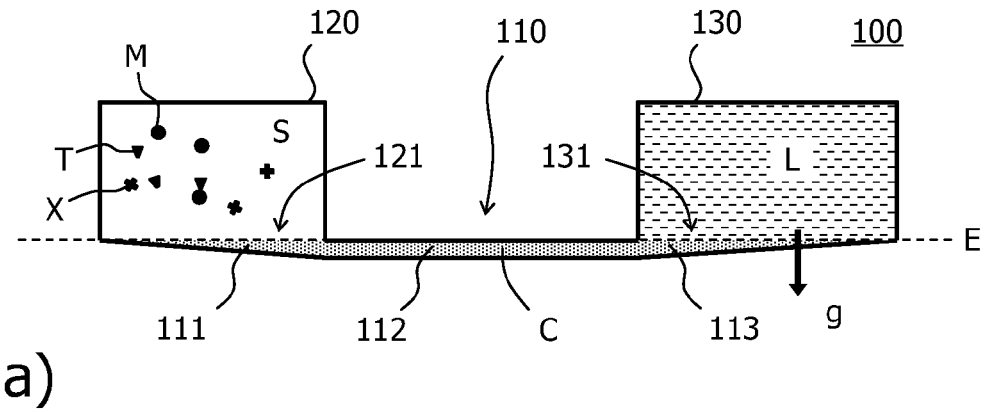
FIG. 3 schematically illustrates a preferred embodiment of the method according to the invention when being executed in an exemplary apparatus according to the invention.
Figure 3:
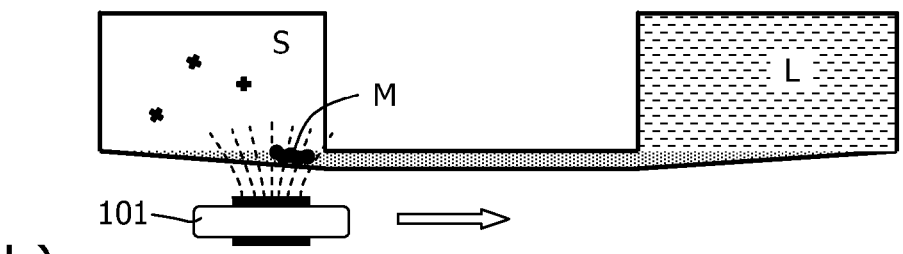
Figure 3:
Figure 3:
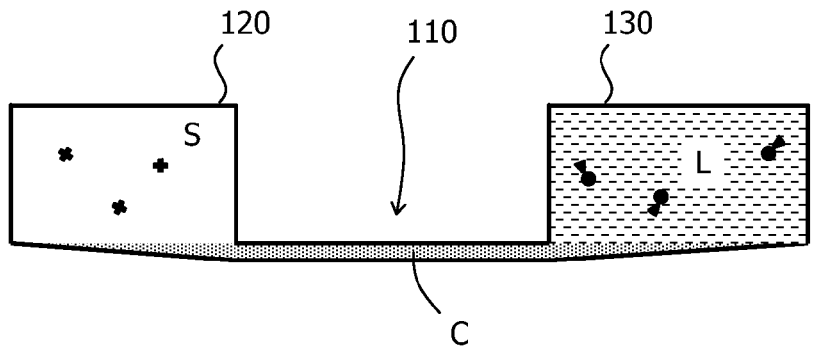

A particular embodiment of such an integrated apparatus 100 is illustrated in a sectional side view in FIG. 3. The apparatus 100 comprises the following components:

A sample chamber 120. Though not shown in the Figure, the sample chamber 120 will typically be connected to other components of the device, for example an inlet, by corresponding channels.

A carrier chamber 110 that is arranged below the sample chamber 120 (in the shown typical arrangement of the apparatus 100 relative to the force of gravity, g). This means that there is a (horizontal) plane E such that the sample chamber 120 is completely above and the carrier chamber 110 is completely below this plane (which, by definition, extends infinitely). Accordingly, the "inlet interface" 121 between the sample chamber 120 and the carrier chamber 110 lies within said plane E. The carrier chamber 110 comprises a first compartment 111 that lies below the sample chamber 120, adjacent to the inlet interface 121. Furthermore, the carrier chamber 110 comprises a channel portion 112 that connects the first compartment 111 to a second compartment 113 below the third chamber 130 which is explained next.

A third chamber 130 that is disposed at the other end of the aforementioned channel portion 112 of the carrier chamber 110 and that has a similar design as the sample chamber 120. In the shown embodiment, the whole third chamber 130 is located above the plane E, wherein an "outlet interface" 131 lies within the plane E and constitutes the interface towards the second compartment 113 of the carrier chamber 110.

With the described apparatus 100, the following sequence of steps can be executed as illustrated in FIG. 3 a)-d):

a) Providing a sample S with magnetic particles M in the sample chamber 120. Moreover, the carrier chamber 110 is filled with a carrier C, e.g. a fluorocarbon, while the third chamber 130 is filled with some further agent L. As the sample S and the agent L are immiscible with the carrier C, the different phases separate and contact each other at the inlet interface 121 and the outlet interface 131, respectively.

b) Magnetic particles M are pulled with the help of a magnet 101 from the sample S into the first compartment 111 of the carrier chamber 110, where they form a cluster.

c) By moving the magnet 101 along the channel 112 to the second compartment 113 below the third chamber 130, the cluster of magnetic particles M is moved accordingly. Instead of actually moving a magnet 101, it would of course also be possible to only change the magnetic field generated by a stationary field generator (e.g. an electromagnet) and/or to establish a static magnetic field (gradient) along the channel 112. Due to the proximity of the walls in a microfluidic setting, care has to be taken in the carrier chamber to avoid wetting of the channel by the aqueous phase. This can for example be achieved by geometrical transitions which hamper wetting or by using hydrophobic channel walls.

d) By switching the magnetic field off (or by removing the magnet 101), the magnetic particles M are released and disperse readily into the reagent L, which may for example be a buffer solution. Further processing steps can then be added to continue the assay.

The magnetic beads M and the carrier C can be provided with the sample S in different forms, e.g. as separate entities which are mixed together randomly by shaking, or stepwise by first introducing the carrier followed by the magnetic beads in a water-based solution, like buffer, or by first introducing the magnetic beads and then adding this mixture to a carrier layer in a reservoir, etc. If the sample is introduced with the magnetic beads M and the carrier C already mixed externally, the carrier phase will spontaneously gather at the bottom of the container covering the lowest part where the first compartment 111 of the carrier chamber 110 is located.

Alternatively, the fluidic system can be prefilled with carrier C. A carrier like a fluorocarbon is non volatile and does not diffuse through the walls, which allows for a long shelf life. A particular way is to provide the FC material in the form of discrete well controlled droplets by a special microfluidic arrangement.

Also the magnetic beads M may optionally be stored in the apparatus 100. Magnetic actuation schemes can be used for mixing the magnetic beads with the sample solution for incubation before they are pulled into the carrier phase.

As an alternative to the active transport with a magnet 101, the carrier phase containing the magnetic particle cluster can be transported conventionally, e.g. by opening some valve (not shown).

In the following, a particular example will be described that was executed with a cartridge resembling that of FIG. 3, but with a stepwise transition in the carrier chamber instead of the inclined bottom. Carboxylated beads were dispersed in demi water. Fluorocarbon FC 40 (available from 3M) was inserted in the cartridge in a quantity to just fill the connecting channel and part of the bottom of the reservoir. The bead solution was added to it. Since the FC 40 has a much higher density, it formed a bottom layer. Upon moving a permanent magnet underneath the solution, the water phase was pulled down slightly so that an inclined interface was formed. The magnetic beads assembled in the water phase until they reached a certain density upon which the cluster of beads was pulled into the FC phase.

Upon moving the magnet in the direction of the channel, the cloud of magnetic beads followed and formed a completely isolated hydrophilic cluster in the hydrophobic FC matrix. This cluster could be moved at very low resistance through the low viscosity FC fluid to the exit of the channel without dragging water along. At the exit, the beads could be pulled back into the water phase.

In a second experiment the transition at the entrance was done in a different way so that a tail of water was dragged along with the cluster of beads at the interface. The tail stayed attached to the beads but lost connection to the reservoir of origin. This aspect is important for minimizing the amount of potential impurities which might be attached to the bead cluster for purification steps in a biological assay.

In summary, it is proposed to use carriers like liquid fluorocarbons (FC) in combination with actuated magnetic beads for sample preparation to replace washing steps. Magnetic beads may be used for selective capture of cells or bio-molecules from a biological sample. The carrier liquid and magnetic beads are mixed with the sample. The carrier forms a continuous layer underneath the typically water-based sample volume. The beads are pulled into the carrier leaving all impurities behind in the sample. The carrier typically has a much higher density and is immiscible with the sample, and the impurities are totally immiscible with carrier. The beads and (part of) the carrier can then be transported actively into the next section for continuing the assay. The system is simple, gravity based. No surface tension dependent processing and/or shelf life issues occur. The interface between sample and carrier phase can be made large to have efficient transfer. A carrier like FC can be mixed into the sample and will phase separate automatically to form a bottom layer.

The apparatuses and methods according to the invention can for example be applied as biosensors, in sample preparation for molecular diagnostics (for infectious diseases, oncology etc.), in immuno-sensing, in a lab-on-a-chip, or in point-of-care testing.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for extracting magnetic particles from a liquid sample, the method comprising acts of:
    mixing the liquid sample, the magnetic particles and a liquid carrier, the liquid carrier being immiscible with the liquid sample and having another mass density than the liquid sample;
    ceasing of the mixing act to allow for a sedimentation of the liquid carrier under an influence of gravity; and
    generating a magnetic field that moves the magnetic particles from the liquid sample into the liquid carrier.

2. The method according to claim 1, wherein the magnetic particles are further transferred from the liquid carrier into another material.

3. The method according to claim 1, wherein the magnetic particles in the liquid carrier are aspirated by a transfer device.

4. The method according to claim 1, wherein after the generating act the liquid sample that has not been moved into the liquid carrier is aspirated by a transfer device leaving behind the liquid carrier and the magnetic particles.

5. The method according to claim 1, wherein at least a component of a movement of the magnetic particles from the liquid sample into the liquid carrier is parallel to a direction of gravity.

6. The method according to claim 1, wherein the magnetic particles can be moved by a magnetic field through the liquid carrier to a target zone.

7. The method according to claim 1, wherein the liquid carrier has a higher mass density than the liquid sample.

8. The method according to claim 1, wherein the liquid carrier comprises at least one component selected from the group consisting of halogenated oils, hydrocarbons, and alkanes.

9. The method according to claim 1, wherein the magnetic particles are non-wetting with respect to the liquid carrier.

10. The method according to claim 1, wherein the magnetic particles can specifically bind components of the liquid sample.

11. The method according to claim 8, wherein the halogenated oils are preferably at least one of a fluorocarbons, a perfluorocarbons and a silicone oils, and wherein the hydrocarbons are preferably at least one of an aliphatic hydrocarbon and an aromatic hydrocarbon.

12. The method according to claim 1, wherein the liquid carrier is at least one of a hydrocarbon oil and an alkane oil.

13. The method according to claim 1, wherein a ratio of mass densities between the liquid sample and the liquid carrier is larger than at least one of 1 to 1.05, 1 to 1.15 and 1 to 1.3.

14. The method according to claim 1, wherein moving the magnetic particles from the liquid sample into the liquid carrier via the generating of the magnetic field is independent of surface tension.

* * * * *